United States Patent [19]

Akhavi

[11] 4,240,425
[45] Dec. 23, 1980

[54] SYRINGE WITH PLUG TYPE NEEDLE HUB LOCK

[75] Inventor: David S. Akhavi, Los Angeles, Calif.

[73] Assignee: American Hospital Supply Corporation, Evanston, Ill.

[21] Appl. No.: 953,608

[22] Filed: Oct. 23, 1978

[51] Int. Cl.³ .............................................. A61M 5/00
[52] U.S. Cl. ................................ 128/218 N; 128/221
[58] Field of Search ............... 128/218 R, 218 N, 215, 128/216, 221; 206/365

[56] References Cited

U.S. PATENT DOCUMENTS

| 3,021,942 | 2/1962 | Hamilton | 206/365 |
| 3,043,304 | 7/1962 | Higgins | 128/218 N |
| 3,112,747 | 12/1963 | Cowley | 128/218 R |
| 3,179,107 | 4/1965 | Clark | 128/221 |
| 3,370,588 | 2/1968 | Burke | 128/221 |
| 3,380,450 | 4/1968 | Adelberger | 128/218 R |
| 3,712,302 | 1/1973 | Burke et al. | 128/221 |
| 4,040,421 | 8/1977 | Young | 128/218 N |

Primary Examiner—John D. Yasko
Attorney, Agent, or Firm—Larry N. Barger

[57] ABSTRACT

A needle hub with an internal plug and an external skirt which wedgingly squeeze a tubular syringe adapter therebetween to permanently lock the needle to the adapter. The adapter is of a softer material (polypropylene) than the hub (polycarbonate) and includes longitudinal crush ribs that frictionally lock the adapter and hub together while providing a sterilizing gas vent into the adapter-hub joint.

13 Claims, 4 Drawing Figures

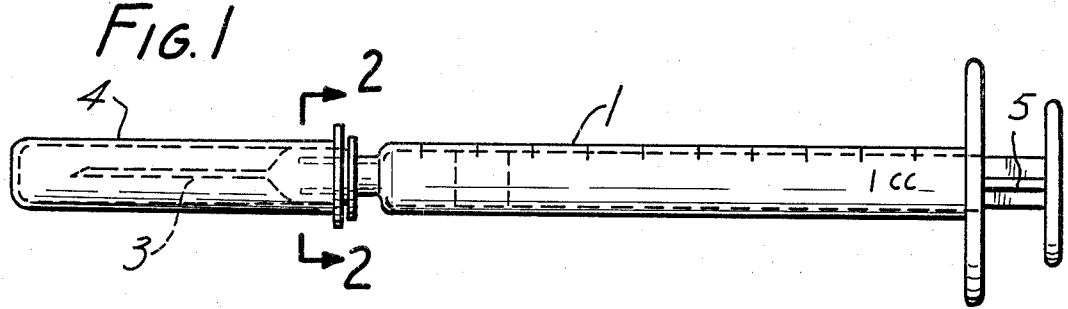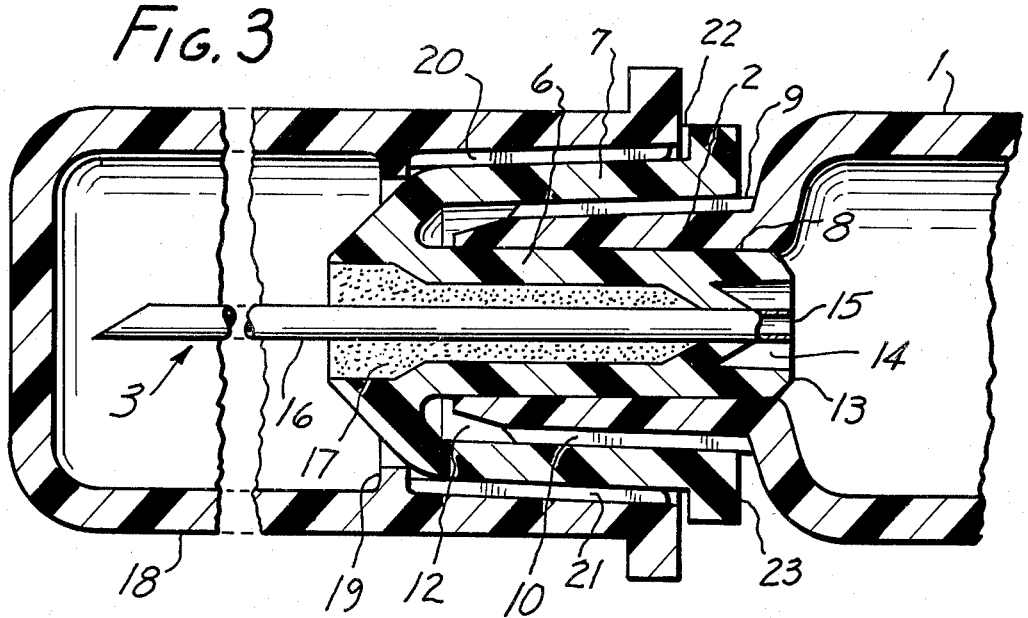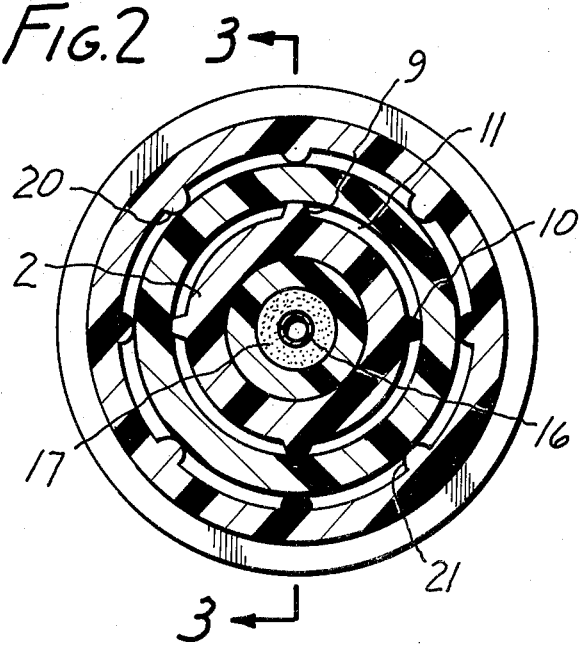

SYRINGE WITH PLUG TYPE NEEDLE HUB LOCK

BACKGROUND

In my related co-pending application, Syringe Coupling System, Ser. No. 953,609, filed Oct. 23, 1978, I describe a needle hub with improved frictional retention to an outer surface of a syringe adapter. Such hub is adapted to be twistingly removed from the syringe by a wrenching structure on a needle protector.

The present invention relates specifically to an improved coupling between a "plug type" needle hub that forms a liquid-tight seal on an inner surface of a syringe adapter. The hub is intended to be permanently secured to such adapter by an external skirt that squeezes the tubular adapter between the skirt and plug of the hub. Such structure is very useful for low capacity (1cc) syringes used to inject insulin. The plug prevents loss of any significant amount of insulin within the tubular adapter.

A previous plug type hub structure for a low capacity insulin syringe is described in U.S. Pat. No. 4,040,421. Here the external gripping skirt of the hub includes an annular lateral circumferential rib 54 that grips the syringe adapter. However, this rib 54 has disadvantages in that (1) it prevents sterilizing gases from entering a molding tolerance pocket at 16 which might become contaminated during a manufacturing process, and (2) it is difficult to mold because a lateral rib tends to distort when longitudinally stripped from its mold. Also, the hub is of a relatively soft polypropylene material for ease of assembly and moldability. A polypropylene skirt of the hub has limited dimensional stability and can slightly expand due to cold flow during long term storage, thereby loosening its grip.

A transverse rib was believed necessary between the hub skirt and syringe adapter to get any significant frictional retaining force. U.S. Pat. No. 3,043,304 describes spirally cutting threads in longitudinal ribs to get a thread interlock for holding power. A longitudinally extending rib would be expected to freely pull off at the syringe adapter because there were no lateral shoulders in either the hub skirt or the syringe adapter. Such longitudinal ribs have been used in "pull off" needle protectors, as described in U.S. Pat. No. 3,121,747.

The applicant unexpectedly found that longitudinal ribs do provide a very firm retaining lock on a plug-type hub where the hub and syringe adapter have substantially different hardnesses.

SUMMARY OF THE INVENTION

The present invention overcomes the problems with previous plug-type needle hubs by providing at least one longitudinally extending crush rib between an external skirt of a plug-type needle hub and a tubular syringe adapter. The crush rib provides a spacer for a sterilizing gas vent into a tolerance control gap adjacent a forward end of the syringe adapter. The longitudinally extending rib helps prevent rotational movement of the hub relative to the syringe adapter, and is preferably integrally formed on an exterior surface of a polypropylene syringe adapter where it can wedgingly engage an outer skirt of a dimensionally stable harder polycarbonate needle hub.

THE DRAWINGS

FIG. 1 is a side elevational view of the syringe;

FIG. 2 is an enlarged sectional view taken along line 2—2 of FIG. 1;

FIG. 3 is a sectional view taken along line 3—3 of FIG. 2; and

FIG. 4 is a further enlarged sectional view showing a longitudinal crush rib profile on the syringe's tubular adapter.

DETAILED DESCRIPTION

FIG. 1 shows a syringe of 1cc capacity for use for insulin injection or the like and includes a barrel 1 with the forward tubular adapter 2. A needle, generally shown at 3, is mounted to adapter 2, and such needle is encased by a protector 4. A typical reciprocal plunger 5 is shown within barrel 1.

In the sectional view at FIGS. 2 and 3, it is seen that adapter 2 has its tubular wall sandwiched between a central hub plub 6 and an external skirt 7. The liquid-tight seal between the adapter 2 and needle hub is made at surface 8; i.e., internally of adapter 2. The adapter includes a series of integral upstanding crush ribs 9 and 10 on its outer surface. These ribs extend longitudinally and are preferably approximately parallel to a longitudinal axis of the syringe adapter and needle hub. Between crush ribs, such as 9 and 10, are vent passages, such as 11, for sterilizing gases to enter an annular tolerance pocket 12 adjacent a forward end of adapter 2. Thus, all internal portions of the hub and syringe joint are sterilizable.

The needle hub's plug 6 extends to a rearward end 13 so as to block out nearly all of the lost volume area within adapter 2. A small pocket 14 can be provided to insure that with molding and assembly tolerances the rear portion 15 of cannula 16 will not be blocked by thermoplastic material at a rear end of the hub post 6. Epoxy 17 secures the cannula 16 to hub post 6.

During assembly, preferably the hypodermic needle, shown generally at 3, which includes both the hub and cannula, is preassembled to a protector 18 and bottoms out against a stop ring 19. Stop ring 19 can have appropriate gates (not shown) for sterilizing gas passage along gaps between longitudinal ribs 20 and 21 on an inner surface of protector 18. Also, it is desirable to include one or more grooves 22 on a forward surface of flange 23 to provide a vent structure for sterilizing gases to flow inside protector 18.

In FIG. 4, the adapter 2 is shown with its integral upstanding longitudinally extending rib, shown as 9. Preferably, this adapter is of a relatively soft polypropylene thermoplastic material of a Rockwell hardness of R 80-110 that can crushably deform (and still provide sterilizing vent structure) upon wedge staking of the combined needle protector 18 and needle 3 on adapter 2. Preferably, the hub is of a much harder and more dimensionally stable material than the polypropylene syringe adapter. A polycarbonate hub of a Rockwell hardness of R 115 and 125 has been found to work exceptionally well when combined with a longitudinally extending crush rib structure on the syringe adapter. This is exceptionally unexpected in that longitudinal ribs are normally thought to aid rather than inhibit axial pull off as is exhibited in the longitudinal rib structure of protector 18 which does readily pull off. It has been found that longitudinal ribs work in this unexpected fashion when they are internal to the sandwich structure of the hub-syringe adapter-hub as shown in FIGS. 2 and 3. Such hub is intended to permanently lock to the adapter and not be manually removable.

In the foregoing description, a specific example has been used to describe the invention. However, it has been understood by those skilled in the art that certain modifications can be made to this example without departing from the spirit and scope of the invention.

I claim:

1. A syringe coupling system with a hub having an internal plug and an external skirt permanently securing a tubular syringe adapter therebetween, wherein the improvement comprises: a longitudinally extending rib capable of longitudinal strip ejection from a mold without substantial distortion on one of the hub and adapter wedgingly secured against the other; and said plug and skirt are spaced sufficiently close to each other to grippingly force the longitudinal rib against the hub or adapter to prevent longitudinal separation of the hub and adapter by manual force during use.

2. A syringe coupling system as set forth in claim 1, wherein the rib is on the syringe adapter.

3. A syringe coupling system as set forth in claim 2, wherein the rib is integral with the syringe adapter and on its external surface wedgingly secured against an internal surface of the hub skirt.

4. A syringe coupling system as set forth in claim 1, wherein the syringe adapter has a forward end and the adapter and hub define an internal tolerance gap therebetween with a sterilizing gas vent extending along said rib.

5. A syringe coupling system as set forth in claim 1, wherein said one of the hub and adapter that includes the rib is of a substantially softer material than the other.

6. A syringe coupling system as set forth in claim 5, wherein the rib is of a polypropylene material having a Rockwell hardness of R 80 to 110.

7. A syringe coupling system as set forth in claim 5, wherein the other of the hub and adapter is of a polycarbonate material having a Rockwell hardness of R 115 to 125.

8. A syringe coupling system as set forth in claim 1, wherein the syringe coupling system includes an axially removable protector enclosing the hub, and said hub supports a cannula.

9. A syringe coupling system as set forth in claim 8, wherein the protector includes longitudinally extending ribs forming a sliding pull off structure.

10. A syringe coupling system as set forth in claim 1, wherein there are a plurality of circumferentially spaced ribs about an external surface of the syringe adapter.

11. A syringe coupling system with a hub having an internal plug and an external skirt permanently securing a tubular thermoplastic syringe adapter therebetween, wherein the improvement comprises: an upstanding crushable longitudinally extending spacer capable of longitudinal strip ejection from a mold without substantial distortion, which spacer is integral with the syringe adapter for permanently locking the hub and adapter together; and said plug and skirt are spaced sufficiently close to each other to grippingly force the longitudinally extending spacer against the hub to prevent longitudinal separation of the hub and adapter by manual force during use.

12. A syringe coupling system as set forth in claim 11, wherein the spacer is crushed against the hub's external skirt.

13. A syringe coupling system as set forth in claim 11, wherein there are a plurality of such spacers circumferentially spaced around the adapter.

* * * * *